United States Patent [19]

Jacquet et al.

[11] Patent Number: 4,803,228
[45] Date of Patent: Feb. 7, 1989

[54] UNSATURATED AROMATIC PEROXIDES AND THEIR USE IN PHARMACEUTICAL AND COSMETIC COMPOSITIONS

[75] Inventors: Bernard Jacquet, Antony; Michel Hocquaux, Paris; Didier Semeria, Gif Sur Yvette; Didier Saint-Leqer, Paris, all of France

[73] Assignee: L'Oreal, Paris, France

[21] Appl. No.: 102,492

[22] Filed: Sep. 29, 1987

[30] Foreign Application Priority Data

Sep. 30, 1986 [FR] France ................... 86 13606

[51] Int. Cl.⁴ ................ A61K 31/075; C07C 179/18; C07C 179/00
[52] U.S. Cl. ................ 514/714; 260/502 R; 514/859; 514/24; 514/29; 568/566
[58] Field of Search ........ 568/566; 560/302; 260/502 R; 514/714

[56] References Cited

U.S. PATENT DOCUMENTS 3,535,422 10/1970 Cox et al. .................. 424/164
3,558,665 1/1971 Friedman .................. 260/348

Primary Examiner—Paul Lieberman
Assistant Examiner—Kathleen Markowski
Attorney, Agent, or Firm—Cushman, Darby & Cushman

[57] ABSTRACT

A peroxide having an aromatic radical and an unsaturated group has the formula

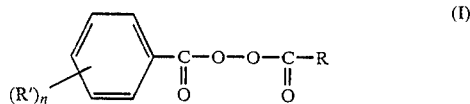

wherein R represents linear or branched, mono- or polyunsaturated alkenyl having 5 to 21 carbon atoms or cycloalkenyl having 5 to 10 carbon atoms, n is 1 or 2 and R' represents hydrogen, halogen, —CF$_3$, methoxy, ethoxy or acyl having 2 to 16 carbon atoms.

The peroxide is employed in pharmaceutical or cosmetic compositions for the treatment of various dermatoses, and especially for the treatment of acne.

14 Claims, No Drawings

UNSATURATED AROMATIC PEROXIDES AND THEIR USE IN PHARMACEUTICAL AND COSMETIC COMPOSITIONS

BACKGROUND OF THE INVENTION

The present invention relates to new peroxides having an aromatic group and an unsaturated group, and to their use in therapeutic or cosmetic compositions for the treatment of various dermatoses, and principally for the treatment of acne.

Acne, as is well known, is a cutaneous disorder, polymorph (several types of lesions existing in a given person) occurring generally at puberty and disappearing spontaneously in the majority of cases at about age 20 to 25.

Acne if found, more particularly, in areas rich in sebaceous glands, which evidences a certain dependence of this dermatosis vis-a-vis sebum, a synthesis project of the gland.

The increase in hormonal activity occuring at puberty, causes a hyperactivity of the sebaceous glands and the sebum thus generated flows then towards the cutaneous surface by the pilosebaceous duct.

The ethiopathogenesis of acne, although poorly defined, finds its origin in the formation of a characteristic lesion, the comedo, which results in the obstruction of the pilosebaceous duct as a result of diskeratinization of the zone of the infundibilium of the duct.

This obstruction has for a major effect a modification of the viscosity of the sebum and the physico-chemical characteristics of the environment (pH, oxygen vapor pressure . . . ).

This modification permits hyperproliferation of resident cutaneous strains, principally *Propionibacterium acnes*, anaerobic or aero-tolerant strains.

This bacterial hyperproliferation has for a consequence the liberation in the environment of certain proteases of bacterial origin which cause a lysis of the follicular sac and thus the liberation of inflammatory compounds in the dermis which in turn effects an inflammatory type reaction of the organism.

The essential elements of the pathology of acne are then:

an increase in sebaceous excretion,
a disorder in the keratinization of the pilosebaceous duct and
a bacterial hyperproliferation, principally of *Propionibacterium acnes*.

A good anti-acne agent capable of treating acne in an effective manner must then exhibit the following activities:

(a) a keratolytic and comedolytic activity so as to avoid hyperkeratosis of the follicles and to permit removal of comedos, (b) a bacteriostatic activity so as to inhibit the activity of *Propionibacterium acnes* and (c) a sebostatic activity so as to inhibit hyperseborrhea.

Numerous anti-acne agents have been proposed but none can claim to possess all of the activities which are required for the effective treatment of acne and without exhibiting, moreover, secondary or side effects.

Among these known agents, the most well known unquestionably is benzoyl peroxide which is an antibacterial agent also possessing keratolytic properties.

Nonetheless, the use of benzoyl peroxide is not without certain disadvantages due to its instability, its reactivity and its side effects.

Benzoyl peroxide exhibits, as a side effect, a certain aggressiveness capable of causing frequent intolerances during treatment such as itching, and this even when it is employed at relatively weak concentrations.

The present invention provides a new class of anti-acne agents for the treatment of various states of acne using new peroxides exhibiting a kerotolytic, comedolytic and bacteriostatic activity greater than that of benzoyl peroxide.

The present invention relates to peroxides having an aromatic radical and an unsaturated group and having the formula

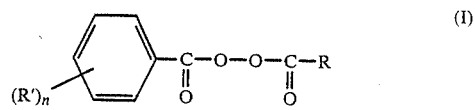

wherein

R represents linear or branched, mono- or polyunsaturated alkenyl having 5 to 21 carbon atoms or cycloalkenyl having 5 to 10 carbon atoms, n is 1 or 2, and R' represents hydrogen, halogen, —CF$_3$, methoxy, ethoxy or acyl having 2–16 carbon atoms.

Pharmacologic studies carried out using these new peroxides have evidenced that they exhibit keratolytic, comedolytic and bacteriostatic activity clearly greater than that of benzoyl peroxide.

In Formula I, above, the aromatic radical is preferably phenyl, p-chlorophenyl, m-chlorophenyl, 2,4-dichlorophenyl, p-methoxy phenyl or o-, m- or p-trifluoromethyl phenyl.

The linear or branched, mono- or poly-unsaturated alkenyl having 5 to 21 carbon above is preferably one of the following:

(1) —CH=CH—CH(CH$_3$)$_2$, i.e. 3-methyl-1-butenyl,
(2) —C(CH$_3$)=CH—CH$_2$—CH$_3$, i.e. 1-methyl-1-butenyl,
(3) —CH=CH—CH—CH$_3$, i.e. 1,3-pentadienyl,
(4) —(CH$_2$)$_4$—CH=CH$_2$, i.e. 5-hexenyl,
(5) —CH=CH—(CH$_2$)$_4$—CH$_3$, i.e. 1-heptenyl,
(6) —(CH$_2$)$_8$—CH=CH$_2$, i.e., 9-decenyl,
(7) —CH=CH—(CH$_2$)$_8$—CH$_3$, i.e. 1-undecenyl,
(8) —(CH$_2$)$_7$—CH=CH—(CH$_2$)$_7$—CH$_3$, i.e. 8-heptadecenyl,
(9) —(CH$_2$)$_7$(CH=CH—CH$_2$)$_2$—(CH$_2$)$_3$, i.e. 8,11-heptadecadienyl and
(10) —(CH$_2$)$_7$—(CH=CH—CH$_2$)$_3$—CH$_3$, i.e. 8,11,14-heptadecatrienyl.

The cycloalkenyl radical having from 5 to 10 carbon atoms in preferably cycohexenyl, cyclopentenyl, norbornenyl or 1,2,3,4,5,6,7,8-octahydronaphthyl.

Among the peroxides of Formula I, above, those preferred which provide particularly satisfactory results in the treatment of various forms of acne are the following:

10-undecenoyl benzoyl peroxide,
6-heptenoyl benzoyl peroxide,
oleoyl benzoyl peroxide, i.e. 9-octadecenoyl benzoyl peroxide and
10-undecenoyl m-chlorobenzoyl peroxide.

The peroxides according to the present invention are obtained in accordance with conventional methods described in the literature and in particular in the following:

"Organic peroxides", Ed. D. Swern, 1970, 1971 and 1972;

K. Rübsamen, Chem. Ber. 102, 1290, (1969);

D. Denney, J. Org. Chem. Vol. 30, 3760, (1965);

The Chemistry of Peroxides, ed. Saul Patai, (1983), John Wiley Sons; and

M. Feldhues-H. J. Schafer, Tetrahedon, 41, (19) 4195–4212 and 4213–4235, (1985).

In accordance with these methods, an unsaturated fatty acid chloride is reacted either with perbenzoic acid or a derivative of perbenzoic acid, in the presence of a base, or with a sodium salt thereof, or even with an aromatic acid chloride, optionally substituted, in the presence of $H_2O_2$ and a base.

Various examples of the preparation of the peroxides according to the invention are given hereafter as an illustration of the invention.

The present invention also relates to pharmaceutical or cosmetic compositions containing, in a pharmaceutically or cosmetically acceptable vehicle or carrier for topical application to the skin at least one peroxide of Formula I as an active component therein.

These compositions can be provided in various forms and principally in the form of an ointment, gel, emulsion, lotion or a stick.

The term "ointment" covers formulations such as creams containing absorbable lipophilic bases, for example, petrolatum, lanolin, polyethylene glycols and mixtures thereof.

The emulsion, be they oil-in-water or water-in-oil emulsions, are prepared by dispersing the peroxides, in accordance with the present invention, in the aqueous phase before emulsification.

The weight ratio of the fatty phase to the aqueous phase in generally between 95:5 and 25:75.

Representative oils capable of constituting the oil or fatty phase include such products as:

(1) animal oils such as lanolin and perhydrosqualene, (2) vegetable oils such as sweet almond oil, avocado oil, ricin oil, olive oil, grapeseed oil, poppy oil, colza oil, peanut oil, corn oil, turnsole oil, hazelnut oil, jojoba oil, safflower oil, wheat germ oil, karite butter and the fat of Shorea robusta; and (3) mineral oils such as paraffin oil, and silicone oils soluble in other oils.

There can also be employed fatty alcohols such as cetyl alcohol or certain synthetic products such as, for example, saturated esters and principally isopropyl palmitate, isopropyl myristate, butyl myristate, cetyl myristate, hexadecyl stearate, glycerol stearate, polyethylene glycol stearate and ethyl palmitate as well as triglycerides of octanoic and decanoic acids, cetyl ricinoleate, purcellin oil and hydrogenated polyisobutylene.

The oily phase of the emulsions can also contain certain waxes and principally carnauba wax, beeswax, ozokerite or candellila wax.

These compositions, in the form of emulsions, can also contain other components such as preservatives, pigments, perfumes, dyes, sunscreen agents, emulsion stabilizers such as magnesium sulfate, filler such as talc, nylon powders, starch or polyethylene, or sequesterants.

However, the carrier or vehicle and components which can react in an undesirable fashion with the peroxides of the present invention must be avoided.

The gels are semi-solid preparations obtained by gelification of a suspension of the peroxides using a gelling agent such as "Bentone gel", sold by N. L. Industries, for an oily phase or for an aqueous phase, crosslinked polyacrylic acid such as that sold by Goodrich under the trade names "CARBOPOL 940" and CARBOPOL 941" and employed in neutralized form or even cellulose derivatives.

If desired, there can be introduced into the gel a nonionic surfactant such as, for example, a polyoxyethylenated alcohol having from 4 to 20 ethylene oxide units or sorbitan esters, which provide a better dispersion and availability of the peroxide.

There can also be incorporated a solvent such as a lower alphatic alcohol, for example, ethanol, in an amount ranging from 0.5 to 30 weight percent, based on the total weight of the composition or a preservative, a perfume or a dye.

The compositions according to the present invention can also include a humectant agent in an amount ranging from 1 to 20 weight percent, based on the total weight of the composition. Representative humectants include glycerine, sorbitol and propylene glycol.

In the compositions, such as described above, the peroxide in accordance with the present invention, is generally present in an amount ranging from 0.1 to 20 weight percent, and preferably from 1 to 10 weight percent, based on the total weight of the composition.

In accordance with a preferred embodiment, the peroxide of the present invention can be combined with at least one topically applicable anti-acne substance, and preferably an antibiotic substance.

In accordance with this embodiment, the antibiotic substance is generally present in an amount ranging from 0.5 to 5 weight percent based on the total weight of the composition.

Representative preferred antibiotics include erythromycin, clindamycin and lincomycin, their esters and their salts.

In accordance with another embodiment, the peroxide according to the present invention can be combined with at least one other keratolytic agent such as, for example, salicylic acid, an anti-fungus agent or anti-inflammatory agent.

In the treatment of acne, the compositions such as defined above are applied at least once a day to the lesions at a rate of 0.5 to 10 mg/cm², the duration of the treatment lasting from about 2 to 14 weeks depending on the severity of the cutaneous disorder.

The following non-limiting examples are given to illustrate the present invention.

A. EXAMPLES OF THE PREPARATION OF PEROXIDES

Example 1

Preparation of 10 undecenoyl benzoyl peroxide

Compound of Formula I wherein $R'=H$ and $R=-(CH_2)_8-CH=CH_2$

To 3.2 grams of sodium perbenzoate (0.02 mole) covered with 50 ml of anhydrous methylene chloride, there are added at $-30°$ C., under an inert gas, 4.46 grams of 10 undecenoic acid chloride (1.1. eq) over a 10 minute period. The reaction mixture is stirred at $-20°$ C. for 2 hours and then washed with a bicarbonate solution until neutral.

After drying the organic phase on sodium sulfate and evaporation of the methylene chloride, in the cold and under a vacuum, 6.2 g of a crude oil are obtained which is then chromatographed on a silica column (eluant: 4/1 mixture of hexane/methylene chloride).

After evaporation of the elution solvent under a vacuum and in the cold, 5.5 g of a pure oil are recovered (91% yield).

The NMR$^1$H spectrum conforms to the expected structure.

IR Spectrum: Bands at $1815^{cm-1}$ and $1785^{cm-1}$ (diacylated peroxide). Band at $1650^{cm-1}$ (vinyl).

Peroxide index: 98.9%.

Example 2

Preparation of 6-heptenoyl benzoyl peroxide

Compound of Formula I wherein R'=H and R=—(CH$_2$)$_4$—CH=CH$_2$

In accordance with the same procedures as those described in Example 1 and by using 3.2 g of 6-heptenoic acid chloride, 4.36 grams of a pure oil are obtained (88% yield).

The NMR$^1$H spectrum conforms to the expected structure.

IR Spectrum: Bands at $1810^{cm-1}$ and $1775^{cm-1}$ (diacylated peroxides). Band at $1640^{cm-1}$ (vinyl).

Peroxide index: 98.2%.

Example 3

Preparation of oleoyl benzoyl peroxide

Compound of Formula I wherein R'=H and R=—(CH$_2$)$_7$—CH=CH—(CH$_2$)$_7$—CH$_3$ In accordance with the same procedures as those described in Example 1 and by using 6.6 g of oleic acid chloride, 6.1 g of a pure oil are obtained (76% yield).

The NMR$^{13}$C spectrum conforms to the expected structure.

IR Spectrum: Bands at $1810^{cm-1}$ and $1775^{cm-1}$ (diacylated peroxides).

Peroxide index: 98.4%.

Example 4

Preparation of 10-undecenoyl-m-chlorobenzoyl peroxide

Compound of Formula I wherein R'=m-Cl, R=—(CH$_2$)$_8$—CH=CH$_2$ and n=1

To 2.6 g of m-chloroperbenzoic acid recrystallized in solution in 70 ml of anhydrous ether, there are added at $-40°$ C., under an inert gas, 3.05 g (1 eq.) of 10-undecenoic acid chloride. After the slow addition of 1.2 ml of pyridine, stirring is continued at $-40°$ C. for about 1 hour.

After washing with water until neutral and drying the organic phase on sodium sulfate, the ether is evaporated under a vacuum and in the cold. 5.2 g of a crude oil are obtained and then the oil is chromatographed on a silica column (eluant: 96/4 mixture of hexane/ethyl acetate). After evaporation of the solution solvent under a vacuum and in the cold, 4.05 g of pure oil are recovered (78% yield).

The NMR$^1$H spectrum conforms to the expected structure.

IR spectrum: Bands at $1820^{cm-1}$ and $1785^{cm-1}$ (diacylated peroxides). Bands at $1650^{cm-1}$ (vinyl).

Peroxide index: 97.3%

EXAMPLES OF COMPOSITION

Example 1

An anti-acne cream having the following composition is prepared:

| | |
|---|---|
| Stearate of polyethylene glycol 50, sold by Atlas under the trade name "MYRJ 53" | 4.00 g |
| Glycerol monostearate | 0.70 g |
| Cetyl alcohol | 2.50 g |
| Self-emulsifiable wax, sold by Henkel under the trade name "SINNOWAX SX" | 4.00 g |
| Petrolatum oil | 10.00 g |
| "Carbopol 940" by Goodrich | 0.20 g |
| Triethanolamine, sufficient amount for pH = 6.5 | 0.20 g |
| 10-undecenoyl benzoyl peroxide | 1.00 g |
| Sodium salt of ethylene diamine tetracetic acid | 0.05 g |
| Water, sufficient amount for | 100.00 g |

Example 2

An anti-acne gel having the following composition is prepared:

| | |
|---|---|
| "Carbopol 934" by Goodrich | 0.60 g |
| Triethanolamine, sufficient amount for pH = 6.5 | 0.40 g |
| Mixture of polyethylene glycol stearate and glycol stearate, sold by Gatefosse under the trade name "TEFOSE 63" | 3.00 g |
| Purcellin oil | 5.00 g |
| 6-heptenoyl benzoyl peroxide | 5.00 g |
| Sodium salt of EDTA | 0.05 g |
| Purified water, sufficient amount for | 100.00 g |

Example 3

An anti-acne stick having the following composition is prepared:

| | |
|---|---|
| Carnauba wax | 6.00 g |
| Ozokerite | 6.00 g |
| Cetyl alcohol | 2.00 g |
| Anhydrous lanolin | 9.50 g |
| Hydrogenated polyisobutylene | 60.00 g |
| Titanium oxide | 2.00 g |
| Red iron oxide | 2.00 g |
| Yellow iron oxide | 1.50 g |
| Brown iron oxide | 1.00 g |
| 10-undecenoyl m-chlorobenzoyl peroxide | 10.00 g |

What is claimed is:

1. A peroxide having an aromatic radical and an unsaturated radical and having the formula

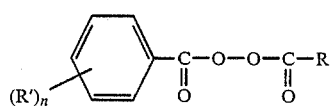

(I)

wherein
R represents linear or branched, polyunsaturated alkenyl having 5 to 21 carbon atoms or cycloalkenyl having 5 to 10 carbon atoms or monounsaturated alkenyl having 5 to 21 carbon atoms selected from the group consisting of 3-methyl-1-butenyl, 1-methyl-1-butenyl, 5-hexenyl, 1-heptenyl, 9-decenyl and 1-undecenyl, n is 1 or 2 and R' represents hydrogen, halogen, —CF$_3$, methoxy, ethoxy or acyl having 2 to 16 carbon atoms.

2. The peroxide of claim 1 wherein said aromatic radical is phenyl, p-chlorophenyl, m-chlorophenyl, 2,4-dichlorophenyl, p-methoxyphenyl or o-, m- or p-trifluoromethyl-phenyl.

3. The peroxide of claim 1 wherein said linear or branched, polyunsaturated alkenyl having 5 to 21 carbon atoms is 1,3-pentadienyl, 8,11-heptadecadienyl or 8,11,14-heptadecatrienyl.

4. The peroxide of claim 1 wherein said cycloalkenyl having 5 to 10 carbon atoms is cyclohexenyl, cyclopentenyl, norbornenyl or 1,2,3,4,5,6,7,8-octahydronaphthyl.

5. The peroxide of claim 1 selected from the group consisting of (1) 10-undecenoyl benzoyl peroxide, (2) 6-heptenoyl benzoyl peroxide and (3) 10-undecenoyl m-chlorobenzoyl peroxide.

6. A pharmaceutical or cosmetic composition comprising in a pharmaceutically or cosmetically acceptable carrier for topical application to the skin, at least one peroxide having an aromatic radical and an unsaturated radical and having the formula:

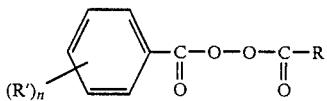

wherein

R represents linear or branched, mono- or polyunsaturated alkenyl having 5 to 21 carbon atoms or cycloalkenyl having 5 to 10 carbon atoms, n is 1 or 2 and R' represents hydrogen, halogen, —CF$_3$, methoxy, ethoxy or acyl having 2 to 16 carbon atoms.

7. The composition of claim 6 wherein said peroxide is present in an amount having from 0.1 to 20 weight percent based on the total weight of said composition.

8. The composition of claim 6 wherein said peroxide is present in an amount ranging from 1 to 10 weight percent based on the total weight of said composition.

9. The composition of claim 6 in the form of an ointment, emulsion, gel, lotion or stick.

10. The composition of claim 6 which also includes at least one antibiotic.

11. The composition of claim 10 wherein said antibiotic is erythromycin, clindamycin, lincomycin, their esters or their salts.

12. The composition of claim 6 which also includes at least one other keratolytic agent, anti-fungus agent or anti-inflammatory agent.

13. The composition of claim 6 which also includes one or more of a preservative, pigment, humectant, perfume, dye, surfactant, thickening agent, filler, solvent, stabilizer, sunscreen agent or sequesterant.

14. A method for treating acne comprising topically applying to the skin of a person suffering from acne an amount, effective for the treatment of acne, of the composition of claim 6.

* * * * *